United States Patent [19]

Schulz et al.

[11] Patent Number: 6,015,458
[45] Date of Patent: Jan. 18, 2000

[54] PROCESS FOR THE PREPARATION OF HIGHLY CHROMATIC PERYLENE PIGMENTS

[75] Inventors: Gregory R. Schulz; Michael J. Greene, both of Mt. Pleasant, S.C.

[73] Assignee: Bayer Corporation, Pittsburgh, Pa.

[21] Appl. No.: 09/211,349

[22] Filed: Dec. 15, 1998

[51] Int. Cl.[7] .................... C07D 221/00; C07D 309/00; C09B 3/14; C09B 3/18
[52] U.S. Cl. ................ 106/498; 106/493; 106/494; 106/499; 546/37
[58] Field of Search ................... 106/493, 494, 106/498, 499; 546/37

[56] References Cited

U.S. PATENT DOCUMENTS

| | | | |
|---|---|---|---|
| 3,357,983 | 12/1967 | Weener et al. | 106/498 |
| 3,615,800 | 10/1971 | Spietschka et al. | 106/493 |
| 3,628,976 | 12/1971 | Stocker | 106/493 |
| 4,431,806 | 2/1984 | Spietschka et al. | 546/37 |
| 4,496,731 | 1/1985 | Spietschka et al. | 546/37 |
| 4,797,162 | 1/1989 | Spietschka et al. | 106/498 |
| 4,992,204 | 2/1991 | Kluger et al. | 252/301.16 |
| 5,076,831 | 12/1991 | Saupe et al. | 71/90 |
| 5,248,774 | 9/1993 | Dietz et al. | 544/125 |
| 5,264,034 | 11/1993 | Dietz et al. | 106/493 |
| 5,466,807 | 11/1995 | Dietz et al. | 546/6 |
| 5,472,494 | 12/1995 | Hetzenegger et al. | 106/493 |

FOREIGN PATENT DOCUMENTS

| | | | |
|---|---|---|---|
| 2001531 | 4/1990 | Canada | 106/498 |
| 0 206 322 | 8/1992 | European Pat. Off. | |
| 1806403 | 10/1970 | Germany | 106/493 |
| 2504481 | 8/1976 | Germany | 106/493 |
| 2803362 | 10/1978 | Germany | 106/493 |
| 3436209 | 4/1986 | Germany | 106/498 |
| 296300 | 11/1991 | Germany | 106/498 |
| 49-125671 | 12/1974 | Japan . | |
| 50-157421 | 12/1975 | Japan . | |
| 50-39735 | 12/1975 | Japan . | |
| 2029440 | 3/1980 | United Kingdom | 106/498 |

OTHER PUBLICATIONS

W. Herbst & K. Hunger, Industrial Organic Pigments, 2nd ed (NY: VCH Publishers, Inc., 1997) (month unavailable) pp. 9 & 476–479.

H. Zollinger, Color Chemistry (VCH Verlagsgessellschaft, 1991)(month unavailable) pp. 227–228 and 297–298.

M.A. Perkins, "Pyridines and Pyridones" in the Chemistry of Synthetic Dyes and Pigments, ed. H.A. Lubs (Malabar, Florida: Robert E. Krieger Publishing Co., 1955) (month unavailable) pp. 481–482.

K. Merkle & H. Schäfer, "Surface Treatment of Organic Pigments" in Pigment Handbook, vol. III (New York: John Wiley & Sons, Inc., 1973), p. 157. (month unavailable).

R.B. McKay, "The Development of Organic Pigments with Particular Reference to Physical Form and Consequent Behavior in Use" in Rev. Prog. Coloration, 10, 25–32 (month unavailable) 1979.

R.B. McKay, "Control of the application performance of classical organic pigments" in JOCCA, 89–93 (month unavailable) 1989.

A.M. El–Naggar et al, Egypt. J. Chem., 24, 127–130 (month unavailable) 1981.

L. Andersen, et al, J. Pharm. Sci., 73, 106–108 (month unavailable) 1984.

J.M. Chapman, Jr. et al, J. Pharm. Sci., 78 903–909 (month unavailable) 1989.

I.H. Hall et al, Acta Pharm. Nord., 2, 387–399 (month unavailable) 1990.

Y.I. Kuznetsov & O.A. Luk'yanchikov, Zasch. Met., 27, 64–71 (month unavailable) 1991, translation attached also.

I.H. Hall et al, Anti–Cancer Drugs, 5, 75–82 (month unavailable) 1994.

P. Erk et al, Eur. Coat. J., 10, 906–910 (month unavailable) 1997.

F. Graser, "Perylenes" in Pigment Handbook, 2nd edition, vol. III, (NY: John Wiley & Sons, Inc. 1988), pp. 653–658. (month unavailable).

A. Streitweiser, Jr. & C.H. Heathcock, Introduction to Organic Chemistry, 3rd edition (NY: Macmillan publishing Company, 1985) (month unavailable) pp. 495 & 866.

*Primary Examiner*—Anthony Green
*Attorney, Agent, or Firm*—Joseph C. Gil; Richard E.L. Henderson

[57] ABSTRACT

This invention relates to a process for preparing perylene pigment compositions by reaction of (a) a perylene tetracarboxylic compound;

(b) about 0.01 to about 20% by weight, relative to the perylene tetracarboxylic compound, of a non-pigmentary cyclic anhydride or imide of formula (I)

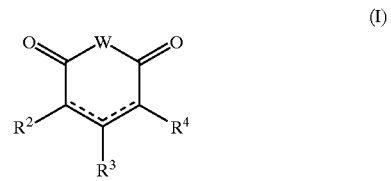

(I)

wherein W is O or $NR^1$ (where $R^1$ is hydrogen, a metal, or optionally substituted alkyl, cycloalkyl, aralkyl, or aryl), $R^2$, $R^3$, and $R^4$ are various combinations of substituents and/or fused-on rings, and the dotted line is an optional double bond representing $R^2$—C=C—$R^3$ or $R^3$—C=C—$R^4$; and (c) ammonia or a primary alkyl, aralkyl, or aryl amine; optionally in the presence of (d) a solvent and/or (e) one or more dispersants.

12 Claims, No Drawings

PROCESS FOR THE PREPARATION OF HIGHLY CHROMATIC PERYLENE PIGMENTS

BACKGROUND OF THE INVENTION

This invention relates to a process for preparing perylene pigment compositions in the presence of certain non-pigmentary cyclic anhydrides or imides. Perylenes, including diimides of perylene-3,4,9,10-tetracarboxylic acid, can be prepared by methods known in the art. E.g., W. Herbst and K. Hunger, *Industrial Organic Pigments,* 2nd ed. (New York: VCH Publishers, Inc., 1997), pages 9 and 476–479; H. Zollinger, *Color Chemistry* (VCH Verlagsgessellschaft, 1991), pages 227–228 and 297–298; and M. A. Perkins, "Pyridines and Pyridones" in *The Chemistry of Synthetic Dyes and Pigments,* ed. H. A. Lubs (Malabar, Fla.: Robert E. Krieger Publishing Company, 1955), pages 481–482; see also U.S. Pat. Nos. 4,431,806, 4,496,731, 4,797,162, 5,248,774, 5,264,034, and 5,466,807. Perylenes as initially isolated in the process of the present invention, often referred to as crude perylenes, are generally unsuitable for use as pigments and thus must be subjected to one or more additional finishing steps that modify particle size, particle shape, and/or crystal structure in such a way that provides good pigmentary quality. See, for example, K. Merkle and H. Schäfer, "Surface Treatment of Organic Pigments" in *Pigment Handbook,* Vol. III (New York: John Wiley & Sons, Inc., 1973), page 157; R. B. McKay, "The Development of Organic Pigments with Particular Reference to Physical Form and Consequent Behavior in Use" in *Rev. Prog. Coloration,* 10, 25–32 (1979); and R. B. McKay, "Control of the application performance of classical organic pigments" in *JOCCA,* 89–93 (1989).

The addition of certain perylene derivatives to the ring-closure step has also been reported. For example, U.S. Pat. No. 5,264,034 discloses the use of certain perylene bisimides or imide-anhydrides to improve the coloristic and rheological properties of perylene pigments. U.S. Pat. No. 5,248,774 discloses certain zwitterionic perylene bis-imide derivatives for use as colorants or as surface-modifying agents for known perylene pigments. U.S. Pat. No. 5,472,494 discloses the use of certain perylene mono-imide derivatives to modify the properties of organic pigments. These patents do not, however, disclose the non-pigmentary cyclic anhydrides and imides of the present invention.

It has now been found that the presence of certain non-pigmentary cyclic anhydrides and imides during the chemical synthesis of perylene bis-imides provides perylene pigment compositions that have improved transparency and color properties, even in the unfinished form that is initially isolated, and that are especially suitable for use in metallic paints.

Non-pigmentary cyclic anhydrides and imides of the type used in the present invention are known. Although some publications have described such compounds as starting materials for dyes (e.g., Japanese Patents 50/157,421, 49/125,671, and 50/39,735), many publications have disclosed purposes completely unrelated to pigment treatment (e.g., U.S. Pat. Nos. 4,992,204 and 5,076,831, European Patent Application 206,322, A. M. El-Naggar et al, *Egypt. J. Chem.,* 24, 127–130 (1981), L. Andersen et al, *J. Pharm. Sci.,* 73, 106–108 (1984), J. M. Chapman, Jr. et al, *J. Pharm. Sci.,* 78, 903–909 (1989), I. H. Hall et al, *Acta Pharm. Nord.,* 2, 387–399 (1990), Y. I. Kuznetsov and O. A. Luk'yanchikov, *Zasch. Met.,* 27, 64–71 (1991), and I. H. Hall et al, *Anti-Cancer Drugs,* 5, 75–82 (1994)).

Substituted naphthalimides are disclosed in a journal article describing computer design of additives for improving the pigment properties of Pigment Red 179, an N,N-disubstituted perylene pigment. P. Erk et al, *Eur. Coat. J.,* 10, 906–910 (1997). The naphthalimides, however, are described as being poor growth inhibitors compared to perylene derivatives. Furthermore, the article does not disclose the incorporation of naphthalimides during pigment synthesis.

SUMMARY OF THE INVENTION

This invention relates a process for preparing perylene pigment compositions comprising reacting (a) a perylene tetracarboxylic compound;

(b) about 0.01 to about 20% by weight (preferably 5 to 15% by weight), relative to the perylene tetracarboxylic compound, of a non-pigmentary cyclic anhydride or imide having the formula (I)

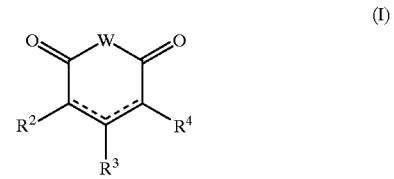

(I)

wherein

W is O or $NR^1$, $R^1$ is hydrogen, a metal, $C_1$–$C_6$ alkyl, $C_5$–$C_8$ cycloalkyl, $C_7$–$C_{16}$ aralkyl, $C_6$–$C_{10}$ aryl, or -Alk-X, $R^2$, $R^3$, and $R^4$ are independently hydrogen, $C_1$–$C_6$ alkyl, $C_7$–$C_{16}$ aralkyl, or $C_6$–$C_{10}$ aryl, or $R^2$ and $R^3$ together are fused-on rings (preferably fused-on cycloalkane or aromatic rings) and $R^4$ is hydrogen, $C_1$–$C_6$ alkyl, $C_7$–$C_{16}$ aralkyl, or $C_6$–$C_{10}$ aryl, or $R^2$, $R^3$, and $R^4$ together are fused-on rings (preferably fused-on cycloalkane or aromatic rings), the dotted line is an optional double bond representing $R^2$—C=C—$R^3$ or $R^3$—C=C—$R^4$ (including a formal double bond of any fused-on aromatic ring formed by $R^2$ and $R^3$ taken together or by $R^2$, $R^3$, and $R^4$ taken together), Alk is $C_1$–$C_{18}$ alkylene or $C_5$–$C_8$ cycloalkylene, and X is (i) an anionic group selected from —$SO_3^-$, —$COO^-$, —$PO_3^=$, —$PO(OR^x)O^-$ (wherein $R^x$ is $C_1$–$C_6$ alkyl), —O—$PO_3^=$, and —O—$PO(OR^y)O^-$ (wherein $R^y$ is $C_1$–$C_6$ alkyl), each such anionic group being electrically balanced with a stoichiometric amount of a cation (preferably a hydrogen, metal, and/or ammonium ion), (ii) a cationic group having the formula —$NR^a R^b R^{c+}$ (wherein $R^a$, $R^b$, and $R^c$ are independently hydrogen, $C_1$–$C_6$ alkyl, $C_7$–$C_{16}$ aralkyl, or $C_6$–$C_{10}$ aryl), each such cationic group being electrically balanced with a stoichiometric amount of an anion (preferably halide, sulfate, phosphate, nitrate, mesylate, or tosylate or, less preferably, hydroxide), (iii) $NR^d R^e$, wherein $R^d$ is hydrogen, $C_1$–$C_6$ alkyl, $C_7$–$C_{16}$ aralkyl, $C_6$–$C_{10}$ aryl, $C_2$–$C_6$ alkanoyl, $C_7$–$C_{11}$ aroyl, or sulfonyl and $R_e$ is hydrogen, $C_1$–$C_6$ alkyl, $C_7$–$C_{16}$ aralkyl, or $C_6$–$C_{10}$ aryl, (iv) $OR^f$, wherein $R^f$ is hydrogen, $C_1$–$C_6$ alkyl, or $C_6$–$C_{10}$ aryl, (v) COOR$^g$, wherein R$^g$ is C$_1$–C$_6$ alkyl, C$_7$–C$_{16}$ aralkyl, or C$_6$–C$_{10}$ aryl,
(vi) sulfonyl, or
(vii) C$_6$–C$_{10}$ aryl; and (c) an equivalent excess, relative to the total amount of components (a) and (b), of ammonia or a primary amine having the formula R$^A$-NH$_2$ wherein R$^A$ is C$_1$–C$_6$ alkyl, C$_7$–C$_{16}$ aralkyl, or C$_6$–C$_{10}$ aryl; optionally in the presence of (d) a solvent and/or
(e) one or more additives.

The invention further relates to perylene pigment compositions prepared in this manner.

DETAILED DESCRIPTION OF THE INVENTION

Perylene tetracarboxylic compounds that can be used for the preparation of the pigmentary perylene compositions of the present invention include various carboxylic acids, carboxylic esters, carboxamides, cyclic anhydrides, and/or cyclic imides of formula (II)

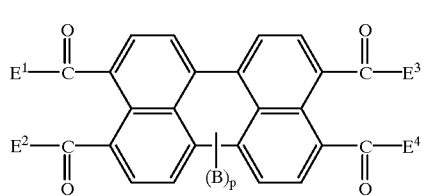

(II)

wherein
E$^1$ and E$^3$ are independently OR or NR'R" and E$^2$ and E$^4$ are independently OR, or E$^1$ and E$^2$ together are O or NA$^1$ and E$^3$ and E$^4$ together are O or NA$^2$, each R is independently hydrogen (i.e., for free acid groups), a metal or ammonium cation (i.e., for salts), C$_1$–C$_6$ alkyl (i.e., for alkyl esters), C$_7$–C$_{16}$ aralkyl (i.e., for aralkyl esters), or C$_6$–C$_{10}$ aryl (i.e., for aryl esters), each R' and R" is independently hydrogen, C$_1$–C$_6$ alkyl, or C$_7$–C$_{16}$ aralkyl, A$^1$ and A$^2$ are independently (but are preferably identically) hydrogen, a metal, C$_1$–C$_6$ alkyl or substituted C$_1$–C$_6$ alkyl, C$_5$–C$_8$ cycloalkyl or substituted C$_5$–C$_8$ cycloalkyl, C$_7$–C$_{16}$ aralkyl or substituted C$_7$–C$_{16}$ aralkyl, or C$_6$–C$_{10}$ aryl or substituted C$_6$–C$_{10}$ aryl, B is C$_1$–C$_6$ alkyl, C$_1$–C$_6$ alkoxy, a sulfonyl group, amino, ammonium, hydroxy, nitro, or halogen, and p is zero or an integer of from 1 to 8.

Preferred perylene tetracarboxylic compounds of component (a) are perylene tetracarboxylic acids and/or esters, as well as salts thereof, in which groups E$^1$, E$^2$, E$^3$, and E$^4$ are independently OH or salt forms thereof or C$_1$–C$_6$ alkoxy (preferably tetracarboxylic acids or salts thereof in which E$^1$, E$^2$, E$^3$, and E$^4$ are identically OH or a corresponding salt form); bis-anhydrides in which E$^1$ and E$^2$ together and E$^3$ and E$^4$together are oxygen atoms; and bis-imides in which E$^1$ and E$^2$ together and E$^3$ and E$^4$together are independently NH or substituted nitrogen atoms (preferably symmetrical bis-imides in which both nitrogen atoms have the same substituent). Preferred perylene tetracarboxylic compounds have no aromatic ring substituents B (i.e., p is zero), but substituted perylene tetracarboxylic compounds in which at least one of the eight substitutable aromatic ring carbon atoms of the perylene moiety has at least one group B (i.e., where p is not zero) are also suitable. Some of the perylene tetracarboxylic compounds used as component (a) can themselves be pigments but it is not necessary for the compounds to be pigments as long as the ultimate perylene pigment composition is pigmentary.

When used to describe the perylene tetracarboxylic compounds of component (a), the term "C$_1$–C$_6$ alkyl" refers to straight or branched chain aliphatic hydrocarbon groups having from 1 to 6 carbon atoms. Examples of C$_1$–C$_6$ alkyl are methyl, ethyl, propyl, butyl, pentyl, hexyl, and the isomeric forms thereof. The term "C$_5$–C$_8$ cycloalkyl" refers to cycloaliphatic hydrocarbon groups having from 5 to 8 carbon atoms. Examples of C$_5$–C$_8$ cycloalkyl are cyclopentyl, cyclohexyl, cycloheptyl, and cyclooctyl. The term "C$_6$–C$_{10}$ aryl" refers to phenyl and 1- or 2-naphthyl. The term "C$_7$–C$_{16}$ aralkyl" refers to C$_1$–C$_6$ alkyl substituted with C$_6$–C$_{10}$ aryl such that the total number of carbon atoms is from 7 to 16. Examples of C$_7$–C$_{16}$ aralkyl are benzyl, phenethyl, and naphthylmethyl. Substituted alkyl groups are those in which one or more carbon atoms are substituted with alkoxy, halogen, hydroxy (including tautomeric oxo forms), alkoxycarbonyl, aryloxycarbonyl, cyano, and nitro as defined herein. Substituted aryl and aralkyl groups are those in which one or more carbon atoms are substituted with alkyl, alkoxy, halogen, hydroxy (including tautomeric oxo forms), alkoxycarbonyl, aryloxycarbonyl, cyano, and nitro as defined herein. The term "C$_1$–C$_6$ alkoxy" refers to straight or branched chain alkyl oxy groups having from 1 to 6 carbon atoms. Examples of C$_1$–C$_6$ alkoxy are methoxy, ethoxy, propoxy, butoxy, pentyloxy, hexyloxy, and the isomeric forms thereof. The term "sulfonyl group" refers to —SO$_2$—R$^i$ groups, such as alkylsulfonyl (in which R$^i$ is alkyl; for example, methylsulfonyl or ethanesulfonyl), arylsulfonyl (in which R$^i$ is aryl; for example, phenylsulfonyl, 1- or 2-naphthylsulfonyl, and substituted forms such as toluenesulfonyl), sulfoxyl and corresponding esters (in which R$^i$ is OH, alkoxy, cycloalkoxy, aralkoxy, aryloxy), and sulfonamides (in which R$^1$ is —NR$^{ii}$R$^{iii}$, wherein R$^{ii}$ and R$^{iii}$ are independently hydrogen, alkyl, cycloalkyl, aralkyl, or aryl). The terms "amino" and "ammonium" refer respectively to —NR$^{iv}$R$^v$ and —NR$^{iv}$R$^v$R$^{vi+}$ in which R$^{iv}$, R$^v$, and R$^{vi}$ are independently hydrogen, C$_1$–C$_6$ alkyl, or C$_7$–C$_{16}$ aralkyl and each ammonium group is electrically balanced with a stoichiometric amount of an anion. The term "halogen" includes fluorine, chlorine, bromine, and iodine.

It is possible to use salt forms of the perylene tetracarboxylic compounds if at least one of groups E$^1$, E$^2$, E$^3$, and E$^4$ of formula (II) represents a carboxylate anion or an imide form. Suitable carboxylic salts are those in which each anionic carboxylate anion is electrically balanced with a 1/n molar equivalents of an n-valent cation M$^{n+}$ (such as Li$^+$, Na$^+$, K$^+$, Mg$^{++}$, Ca$^{++}$, Ba$^{++}$, Al$^{+++}$, or Fe++, or Fe$^{+++}$) or an ammonium ion having the formula R$^I$R$^{II}$R$^{III}$R$^{IV}$N$^+$ (wherein R$^I$, R$^{II}$, R$^{III}$, and R$^{IV}$ are independently hydrogen, C$_1$–C$_6$ alkyl, C$_1$–C$_6$ hydroxyalkyl, or C$_7$–C$_{16}$ aralkyl). In general, free acids in which at least one of E$^1$, E$^2$, E$^3$, and E$^4$ is OH are initially added to the reaction mixture but are converted to corresponding amine salts by an in situ acid-base reaction with the ammonia or primary amine of component (c). Suitable imide salts of formula (II) are perylenes in which at least one of A$^1$ or A$^2$ represents 1/n molar equivalents of an n-valent cation M$^{n+}$ (such as Li$^+$, Na$^+$, K$^+$, Mg$^{++}$, Ca$^{++}$, Ba$^{++}$, Al$^{+++}$, Fe$^{++}$, or Fe$^{+++}$). Such salts are formed whenever imides of formula (II) in which A$^1$ and/or A$^2$ is hydrogen are exposed to strongly basic media, either during the reaction conditions used to prepare the perylene imide or by addition of a strong base.

The perylene tetracarboxylic compounds described above, some of which are crude or conditioned perylene pigments and some of which are precursors of perylene pigment, can be prepared by any of various methods known in the art. E.g., W. Herbst and K. Hunger, *Industrial Organic Pigments,* 2nd ed. (New York: VCH Publishers, Inc., 1997), pages 476–479; H. Zollinger, *Color Chemistry* (VCH Verlagsgessellschaft, 1991), pages 227–228; M. A. Perkins, "Pyridines and Pyridones" in *The Chemistry of Synthetic Dyes and Pigments,* ed. H. A. Lubs (Malabar, Fla.: Robert E. Krieger Publishing Company, 1955), pages 481–482; and F. Graser, "Perylenes" in *Pigment Handbook,* 2nd edition, Vol. III (New York: John Wiley & Sons, Inc., 1988), pages 653–658.

A critical feature of the invention is the use of non-pigmentary cyclic anhydrides or imides of formula (I). The term "non-pigmentary" means that the compounds are substantially colorless or are significantly less highly colored and lack good pigmentary properties in comparison to the perylene tetracarboxylic compounds and perylene pigment compositions with which they are used. That is, suitable cyclic anhydrides or imides of formula (I) would not themselves have practical utility as pigments. The term "substantially colorless" does not mean that the cyclic anhydrides or imides must be absolutely devoid of color in the visible region but instead means only that the compounds are insignificantly colored in comparison to the perylene pigments with which they are used. For example, preferred cyclic anhydrides or imides of formula (I) will exhibit molar absorptivities less (preferably at least about an order of magnitude less) than those of the perylene precursors and perylene pigment compositions with which they are used.

When used to describe the non-pigmentary cyclic anhydrides or imides of component (b) (including the compounds described below), the terms "$C_1$–$C_6$ alkyl", "$C_5$–$C_8$ cycloalkyl", "$C_7$–$C_{16}$ aralkyl", "$C_6$–$C_{10}$ aryl", "$C_1$–$C_6$ alkoxy", "sulfonyl group", "amino", "ammonium", and "halogen" have the same meanings as given above for the perylene tetracarboxylic compounds. The term "$C_1$–$C_{18}$ alkylene" refers to straight or branched chain aliphatic hydrocarbon groups having from 1 to 18 carbon atoms and two sites of attachment. Examples of $C_1$–$C_{18}$ alkylene are methylene, ethylene, propylene, butylene, pentylene, hexylene, and longer hydrocarbon chains, including both linear and branched chain groups. The term "$C_5$–$C_8$ cycloalkylene" refers to cycloaliphatic hydrocarbon groups having from 5 to 8 carbon atoms and two sites of attachment. Examples of $C_5$–$C_8$ cycloalkylene include 1,3-cyclopentylene, 1,4-cyclohexylene, and the like. The term "$C_2$–$C_6$ alkanoyl" refers to straight or branched chain alkanoyl groups having from 2 to 6 carbon atoms. Examples of $C_2$–$C_6$ alkanoyl are acetyl, propanoyl, butanoyl, pentanoyl, hexanoyl, and the isomeric forms thereof. The term "$C_7$–$C_{11}$aroyl" refers to benzoyl and 1- or 2-naphthoyl in which the aryl portion can optionally be substituted as described above for "aryl."

Preferred cyclic anhydrides and imides are those in which $R^2$ and $R^3$ together form fused-on hydrocarbon rings (preferably fused-on cycloalkane and most preferably aromatic ring systems, such as benzene or 1,2- or 2,3-naphthalene) and $R^4$ is hydrogen, $C_1$–$C_6$ alkyl, $C_7$–$C_{16}$ aralkyl, or $C_6$–$C_{10}$ aryl (preferably hydrogen), or in which $R^2$, $R^3$, and $R^4$ together form fused-on multiple hydrocarbon rings (most preferably polyaromatic ring systems, such as 1,8-naphthalene). Each of the fused ring systems can, of course, be ring-substituted, for example, with $C_1$–$C_6$ alkyl, $C_7$–$C_{16}$ aralkyl, $C_6$–$C_{10}$ aryl, $C_1$–$C_6$ alkoxy, sulfonyl, amino, ammonium, and halogen groups such as described above. For compounds of formula (I) in which W is $NR^1$ (i.e., imides), the $R^1$ group is preferably hydrogen, a metal, $C_1$–$C_6$ alkyl, or —Alk—X in which Alk is $C_1$–$C_{18}$ alkylene and X is —$SO_3^-$ or —$COO^-$ electrically balanced with hydrogen or a metal ion.

Particularly preferred cyclic anhydrides and imides include naphthalene compounds of formula (Ia)

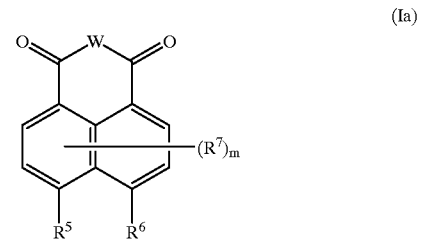

(Ia)

in which W is defined as above; $R^5$ and $R^6$ are independently hydrogen, $C_1$–$C_6$ alkyl, $C_1$–$C_6$ alkoxy, a sulfonyl group, amino, ammonium, hydroxy, nitro, or halogen or $R^5$ and $R^6$ taken together are a group represented by the formula

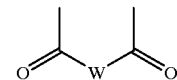

(wherein W is defined as before); each $R^7$ is independently $C_1$–$C_6$ alkyl, $C_1$–$C_6$ alkoxy, a sulfonyl group, amino, ammonium, hydroxy, nitro, or halogen; and m is zero or an integer of from 1 to 4. For compounds of formula (Ia) in which W is $NR^1$ (i.e., imides), the $R^1$ group is preferably hydrogen, a metal, $C_1$–$C_6$ alkyl, or -Alk-X in which Alk is $C_1$–$C_{18}$ alkylene and X is —$SO_3^-$ or —$COO^-$ electrically balanced with hydrogen or a metal ion. Examples of suitable cyclic anhydrides include naphthalic anhydride (i.e., 1,8-naphthalenedicarboxylic anhydride) and 1,4,5,8-naphthalenetetracarboxylic dianhydride. Examples of suitable cyclic imides include naphthalimide (i.e., 1,8-naphthalenedicarboximide), N-methylnaphthalimide, N-(2-sulfoethyl)naphthalimide and salts thereof, N-(2-sulfoethyl)-4-sulfonaphthalimide and salts thereof, and N,N'-bis(2-sulfoethyl)-1,4,5,8-naphthalenetetracarboxylic diimide and salts thereof.

Cyclic anhydrides of formula (I) (where W is O) can be obtained commercially or by conversion of corresponding dicarboxylic acids to the anhydrides using known methods, for example, by heating or by treating with a strong acid or other dehydrating agents. E.g., A. Streitweiser, Jr. and C. H. Heathcock, *Introduction to Organic Chemistry,* 3rd. edition (New York: Macmillan Publishing Company, 1985), pages 495 and 866.

Imides of formula (I) (where W is $NR^1$) can in turn be prepared from corresponding acids, esters, or anhydrides by known methods, preferably by reaction of a corresponding cyclic anhydride with at least a slight molar excess of a suitable amine in a suitable solvent. In a preferred method for preparing imides in which $R^1$ contains no ionic groups, the anhydride and amine react in water heated at about 80° C. to 100° C. at ambient pressure or at temperatures of up to about 140° C. in an autoclave or other sealed reactor, typically for about two to four hours. In a preferred method for preparing imides in which $R^1$ contains anionic groups (e.g., carboxylate, sulfonate, or phosphonate groups), the protonated amino group of the zwitterionic amine precursor is converted into a free amino group by adding an equivalent of a base (such as sodium or potassium hydroxide) to the reaction mixture, after which the reaction is carried out under essentially the same conditions as used for nonionic compounds. However, if the resultant anionic compound is water-soluble, it must be isolated, for example, by acidifying the reaction mixture and isolating the free acid, by increasing the ionic strength of the mixture and isolating the otherwise soluble metal salt (i.e., sodium or potassium), or by precipitating the imide by adding a polyvalent metal salt (e.g., $CaCl_2$, $BaCl_2$, or $FeCl_2$).

Imide salts of formula (I) in which W is $NR^1$ and $R^1$ is a metal can be prepared from corresponding "free" imides in which $R^1$ is hydrogen. Suitable imide salts of formula (I) are those in which each $R^1$ represents 1/n molar equivalents of an n-valent cation $M^{n+}$ (such as $Li^+$, $Na^+$, $K^+$, $Mg^{++}$, $Ca^{++}$, $Ba^{++}$, $Al^{+++}$, $Fe^{++}$, or $Fe^{+++}$). Such salts are formed whenever imides of formula (I) in which $R^1$ is hydrogen are exposed to strongly basic media, either during the reaction conditions used to prepare the perylene imide or by addition of a strong base to the free imide.

Component (c) includes ammonia and primary amines having the formula $R^A$-$NH_2$ in which $R^A$ is $C_1$–$C_6$ alkyl, $C_7$–$C_{16}$ aralkyl, or $C_6$–$C_{10}$ aryl. Examples of suitable primary amines include alkylamines such as methyl amine, ethyl amine, propyl amine, butyl amine, pentyl amine, hexyl amine, and isomeric forms thereof; aralkylamines such as benzylamine and phenethylamine; and arylamines such as aniline, anisidine, phenetidine, toluidine, and various xylidine isomers. It is necessary to use at least a slight excess of ammonia or amine (c) relative to the anhydride and/or imide groups of perylene pigment precursor (a) and non-pigmentary cyclic anhydride or imide (b). In general, about 1.1 to about 10 moles (preferably 1.5 to 5 moles) of ammonia or primary amine (c) is used per mole of the anhydride and imide groups of components (a) and (b). Although generally not preferred, it is possible to use larger quantities of ammonia or primary amine (c), which, if liquid under the reaction conditions, can even serve as solvent or as co-solvent with component (d).

Suitable solvents (d) are liquids that are capable of dissolving or suspending the components of the reaction mixture without significantly decomposing or otherwise reacting during the reaction. Examples of suitable solvents include water; monofunctional alcohols, particularly lower alkanols such as methanol, ethanol, butanol, pentanol, hexanol, and isomeric forms thereof; amides such as dimethylformamide and dimethylacetamide; ketones and ketone alcohols such as acetone and diacetone alcohol; ethers such as tetrahydrofuran and dioxane; alkylene glycols and thioglycols such as ethylene glycol, propylene glycol, butylene glycol, triethylene glycol, hexylene glycol, diethylene glycol, and thiodiglycol; polyalkylene glycols, such as polyethylene glycol and polypropylene glycol; other polyols, such as glycerol and 1,2,6-hexanetriol; lower alkyl ethers of polyhydric alcohols, such as 2-methoxyethanol, 2-(2-methoxyethoxy)ethanol, 2-[2-(2-methoxyethoxy)ethoxy]ethanol, and 2-[2-(2-ethoxyethoxy)ethoxy]ethanol; aromatic and heteroaromatic liquids, such as benzene, pyridine, and quinoline; and other such organic liquids known in the art. Water, methanol, and quinoline are particularly preferred solvents. Other solvents can, of course, also often be used, but it is generally advisable to avoid solvents that can react with the reactive components. The quantity of solvent is generally not critical but should be an amount sufficient to dissolve or suspend the components of the reaction mixture but not so large as to require removal of excessive amounts after the reaction is complete. Typical quantities of solvent range from about 5 to about 20 parts by weight (preferably 7 to 15 parts by weight) relative to the total amount of components (a) and (b).

Solvents (d) may not be necessary if one or more of components (a), (b), or (c) are themselves liquids or if the mixture of components (a), (b), and (c) can be melted without significant decomposition to undesired by-products.

The optional additives (e) can be any of the customary pigment preparation additives known in the art that serve, for example, to improve color properties, lessen or avoid flocculation, increase pigment dispersion stability, and reduce coating viscosity. Suitable additives include, for example, dispersants or surfactants and various pigment derivatives. Examples of suitable dispersants include anionic compounds, such as fatty acids (such as stearic or oleic acid), fatty acid salts (i.e., soaps such as alkali metal salts of fatty acids), fatty acid taurides or N-methytaurides, alkylbenzenesulfonates, alkylnaphthalenesulfonates, alkylphenol polyglycol ether sulfates, naphthenic acids or resin acids (such as abietic acid); cationic compounds, such as quaternary ammonium salts, fatty amines,fatty amine ethylates, and fatty amine polyglycol ethers; and nonionic compounds, such as fatty alcohol polyglycol ethers, fatty alcohol polyglycol esters, and alkylphenol polyglycol ethers. Examples of suitable pigment additives include organic pigments having one or more sulfonic acid groups, sulfonamide groups, carboxylic acid, carboxamide, and/or (hetero)aryl-containing (cyclo)aliphatic groups. Such additives can be incorporated in amounts ranging from about 0.05 to 20% by weight (preferably 1 to 10% by weight), based on the amount of pigment.

The perylene pigment compositions of the present invention can be prepared by mixing components (a), (b), and (c), and optional components (d) and (e) in essentially any sequence. Preferably, however, perylene tetracarboxylic compound (a) and non-pigmentary cyclic anhydride or imide (b), as well as any dispersant (e), are added to solvent (d) and stirred at a temperature of about 0° C. to about 30° C. (preferably at or below room temperature, more preferably 0° C. to 5° C.) before adding ammonia or amine (c). After component (c) is added, the mixture is heated at a temperature of about 50° C. to about 150° C. (preferably 80° C. to 100° C.) until reaction is complete, typically a period of about two to six hours. For example, in particularly preferred embodiments in which component (c) is methylamine, a mixture of the perylene tetracarboxylic compound and the non-pigmentary cyclic anhydride or imide in water is cooled to about 5° C. and then heated with methylamine. Upon completion of the reaction, the reaction mixture is cooled if necessary and the pigment is collected, for example, by filtration, centrifugation, or other known methods.

During the process of the present invention, the ammonia or amine of component (c) may react with acid anhydrides and/or imides that are present in compounds of formulas (I) and/or (II) to form corresponding imides in which at least some of groups $R^1$, $A^1$, and/or $A^2$ are replaced with hydrogen (from ammonia) or group $R^A$ (from amine $R^A$-$NH_2$). However, regardless of whether the starting perylene tetracarboxylic compounds and non-pigmentary cyclic anhydrides or imides are transformed by component (c), the resultant perylene pigment compositions exhibit improved transparency and color properties when compared to perylene pigments prepared in the absence of the non-pigmentary cyclic anhydride or imide.

The pigment composition can optionally be conditioned using methods known in the art, such as solvent treatment or milling in combination with solvent treatment. Final particle size of the pigment can be controlled by varying the method of aftertreatment. For example, pigments can be made more transparent by reducing the particle size or more opaque by increasing the particle size. Suitable milling methods include dry-milling methods such as jet milling, ball milling, and the like, with or without additives, or wet-milling methods such as salt kneading, sand milling, bead milling, and the like in water or organic solvents, with or without additives.

During or after the optional conditioning step, it is often desirable to use various other optional ingredients that provide improved properties. Examples of such optional ingredients include fatty acids having at least 12 carbon atoms, such as stearic acid or behenic acid, or corresponding amides, esters, or salts, such as magnesium stearate, zinc stearate, aluminum stearate, or magnesium behenate; quaternary ammonium compounds, such as tri[($C_1$–$C_4$ alkyl) benzyl]ammonium salts; plasticizers, such as epoxidized soya bean oil; waxes, such as polyethylene wax; resin acids, such as abietic acid, rosin soap, hydrogenated or dimerized rosin; $C_{12}$–$C_{18}$-paraffin-disulfonic acids; alkylphenols; alcohols, such as stearyl alcohol; amines, such as laurylamine or stearylamine; and aliphatic 1,2-diols, such as dodecane-1,2-diol. Such additives can be incorporated in amounts ranging from about 0.05 to 20% by weight (preferably 1 to 10% by weight), based on the amount of pigment. The pigment compositions can also be blended (preferably by dry blending) with one or more pigment derivatives known in the art, particularly sulfonic acid, sulfonamide, and phthalimide derivatives.

Because of their light stability and migration properties, the perylene pigment compositions according to the present invention are suitable for many different pigment applications. For example, pigment compositions according to the invention can be used as the colorant (or as one of two or more colorants) for very lightfast pigmented systems. Examples include pigmented mixtures with other materials, pigment formulations, paints, printing ink, colored paper, or colored macromolecular materials. The term "mixtures with other materials" is understood to include, for example, mixtures with inorganic white pigments, such as titanium dioxide (rutile) or cement, or other inorganic pigments. Examples of pigment formulations include flushed pastes with organic liquids or pastes and dispersions with water, dispersants, and, if appropriate, preservatives. Examples of paints in which pigments of this invention can be used include, for example, physically or oxidatively drying lacquers, stoving enamels, reactive paints, two-component paints, solvent-or water-based paints, emulsion paints for weatherproof coatings, and distempers. Printing inks include those known for use in paper, textile, and tinplate printing. Suitable macromolecular substances include those of a natural origin, such as rubber; those obtained by chemical modification, such as acetyl cellulose, cellulose butyrate, or viscose; or those produced synthetically, such as polymers, polyaddition products, and polycondensates. Examples of synthetically produced macromolecular substances include plastic materials, such as polyvinyl chloride, polyvinyl acetate, and polyvinyl propionate; polyolefins, such as polyethylene and polypropylene; high molecular weight polyamides; polymers and copolymers of acrylates, methacrylates, acrylonitrile, acrylamide, butadiene, or styrene; polyurethanes; and polycarbonates. The materials pigmented with the perylene pigment compositions of the present invention can have any desired shape or form.

The pigment compositions according to this invention are highly water-resistant, oil-resistant, acid-resistant, lime-resistant, alkali-resistant, solvent-resistant, fast to overlacquering, fast to over-spraying, fast to sublimation, heat-resistant, and resistant to vulcanizing, yet give a very good tinctorial yield and are readily dispersible (for example, in plastic materials).

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

Test Methods

Water-based paints tests were carried out on N,N'-dimethylperylenetetracarboxylic diimide prepared according to the invention using a waterborne basecoat/solventborne clearcoat paint system. Untreated N,N'-dimethylperylenetetracarboxylic diimide made by the same method was used as a control. Aqueous dispersions were prepared using a mixture of 12.4% AROLON® 559-G4-70 acrylic resin (Reichhold Chemicals, Inc.), 3.2% SOLSPERSE® 27000 hyperdispersant (Zeneca, Inc.), 1.6% 2-amino-2-methyl-1-propanol (Angus Chemical), and 18% pigment, which gave a pigment-to-binder ratio of 18:12 and a total solids content of 30%. The pigment-to-binder ratio was then reduced to 10:40 with additional AROLON® 559-G4-70 acrylic resin (total amount 26%) and 25% CYMEL® 325 melamine/formaldehyde resin (Cytec Industries), which gave a total solids content of 50%. Masstone and transparency measurements were made using films applied at 76 μm and 38 μm wet film thickness, respectively, and allowed to stand at room temperature for fifteen minutes and at 100° C. for five minutes. Clearcoats containing a mixture of 80% of AROPLAZ® 1453-X-50 alkyd resin (Reichhold Chemicals, Inc.) and 20% CYMEL® 325 melamine/formaldehyde resin at a total solids level of 57% were then applied over the basecoat at a 76 μm wet film thickness and allowed to stand at room temperature for fifteen minutes and at 121° C. for fifteen minutes. Transparencies were calculated using the 38 μm films by subtracting the masstone ΔC value measured over a black background from the masstone ΔC value measured over a white background.

Undertone tint paints were prepared from the reduced aqueous dispersions described above having a pigment-to-binder ratio of 10:40 by adding additional AROLON® 559-G4-70 acrylic resin, CYMEL® 325 melamine/formaldehyde resin, and 35% TINT-AYD® CW-5003 white dispersion (Daniel Products Company), which gave a pigment-to-binder ratio of 1:1.1, a total solids content of 55%, and a $TiO_2$-to-pigment ratio of 90:10. Color measurements were made using films applied at 38 μm wet film thickness and allowed to stand at room temperature for fifteen minutes and at 100° C. for five minutes. Clearcoats were then applied and baked as described above.

Metallic paints were prepared from the dispersion described above having a pigment-to-binder ratio of 18:12 using a water-dispersible aluminum pigment (available as HYDRO PASTE® 8726 from Silberline Manufacturing Co., Inc.), AROLON® 559-G4-70 acrylic resin, and CYMEL® 325 melamine/formaldehyde resin in quantities that provided a pigment-to-binder ratio of 1:2, an aluminum-to-pigment ratio of 20:80, and a total solids content of 43%. Color measurements were made using films applied at 38 μm wet film thickness and baked as described above. Clearcoats were then applied and baked as described above.

Starting Materials

The following commercially available cyclic anhydrides and imides were used in the examples, both as component (b) according to the invention and as starting materials for other compounds within the definition of component (b):

(b)(1) naphthalic anhydride (available from Aldrich Chemical Company) having the formula

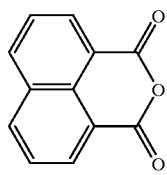

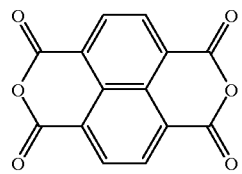

Other cyclic anhydrides and imides used in the examples according to the invention were prepared as described below.

Preparation 1

N-Methylnaphthalimide (cyclic imide (b)(3))

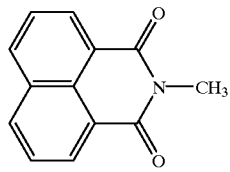

To a suspension of 125.0 g (0.634 mol) of naphthalic anhydride in 1.5 L of water was added 111.5 g (1.44 mol) of a 40% aqueous solution of methylamine. The mixture was then stirred in a sealed autoclave at 145° C. for 5.5 hours and allowed to cool. The resultant precipitate was collected by filtration, washed with water, and dried in an oven at 60° C. to yield 125 g of N-methylnaphthalimide (cyclic imide (b)(3)).

Preparation 2

N-(2-Sulfoethyl)naphthalimide, calcium salt (cyclic imide (b)(4))

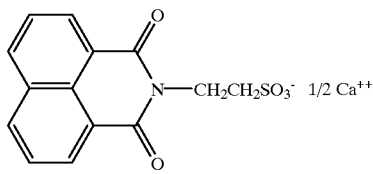

To a suspension of 39.8 g (0.2 mol) of naphthalic anhydride in 1.2 L of water was added 50 g (0.4 mol) of taurine and 26.4 g of 85% potassium flake. The mixture was then stirred in a sealed autoclave at 150° C. for five hours and allowed to cool. To the resultant yellow slurry was added a solution of 40 g of calcium chloride dihydrate in 60 g of water and the mixture was stirred for 30 minutes. The resultant precipitate was collected by filtration, washed with water until free of residual calcium, and dried in an oven at 80° C. to yield 70 g of N-(2-sulfoethyl)naphthalimide as the calcium salt (cyclic imide (b)(4)).

Preparation 3

N-(2-Sulfoethyl)-4-sulfonaphthalimide, barium salt (cyclic imide (b)(5))

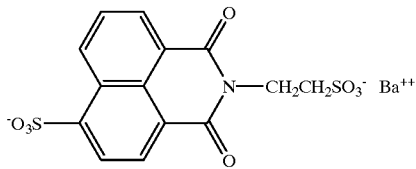

The method of Preparation 2 was repeated except for using 15.8 g (0.05 mol) of the potassium salt of 4-sulfonaphthalic anhydride instead of naphthalic anhydride and 16 g (0.076 mol) of barium chloride instead of calcium chloride dihydrate, yielding 22.1 g of N-(2-sulfoethyl)-4-sulfonaphthalimide as the barium salt (cyclic imide (b)(5)).

Preparation 4

N,N'-Bis(2-sulfoethyl)-1,4,5,8-naphthalenetetracarboxylic diimide, barium salt (cyclic imide (b)(6))

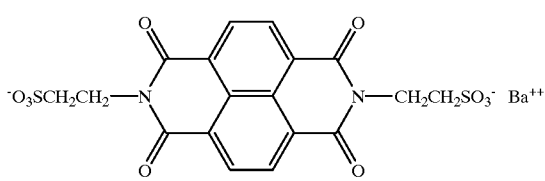

The method of Preparation 2 was repeated except for using 6.7 g (0.025 mol) of 1,4,5,8-naphthalenetetracarboxylic anhydride instead of naphthalic anhydride and 15.6 g (0.075 mol) of barium chloride instead of calcium chloride dihydrate, yielding 10.2 g of N,N'-bis(2-sulfoethyl)-1,4,5,8-naphthalenetetracarboxylic diimide as the barium salt (cyclic imide (b)(6)).

Preparation 5

N,N'-Bis(2-sulfoethyl)-1,4,5,8-naphthalenetetracarboxylic diimide, iron(II) salt (cyclic imide (b)(7))

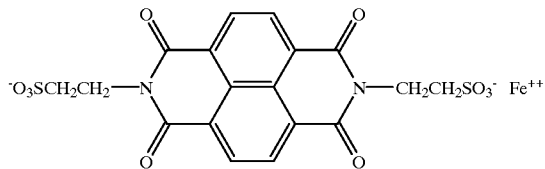

The method of Preparation 4 was repeated except for using 20 g (0.075 mol) of iron(II) chloride instead of calcium chloride dihydrate, yielding 5.45 g of N,N'-bis(2-sulfoethyl)-1,4,5,8-naphthalenetetracarboxylic diimide as the iron (II) salt (cyclic imide (b)(7)).

Example 1

A mixture of 100 g (0.26 mol) of perylene-3,4,9,10-tetracarboxylic dianhydride and 5.4 g (0.027 mol) of naphthalic anhydride was stirred in a mixture of 1000 g of water and 500 g of ice. To the cold (less than 5° C.) slurry was added dropwise 244 g (3.15 mol) of 40% aqueous methylamine over a period of 15 minutes. After being stirred for one hour, during which time the temperature rose to about 15° C., the mixture was heated to 80° C. and held at that temperature for four hours. The reaction mixture was cooled and the crude pigment was filtered and washed with water. To the moist filtercake was added about 10% by weight (based on the pigment) of a high molecular weight copolymer pigment dispersant, a base to adjust to pH 8 to 9, and sufficient water to provide a slurry containing about 10 to about 20% by weight of pigment. The slurry was milled in a horizontal wet mill for eight hours. The milled pigment was removed from the mill and acidified to less than pH 4 using hydrochloric acid. After being stirred for 15 minutes, the pigment was collected by filtration, washed with water until free of acid, and dried in an oven at 80° C. to yield a bright red pigment. Test data for crude pigment are given in Table 1 and test data for milled pigment are given in Table 2.

Examples 2–7

The method of Example 1 was repeated using similar mixtures of perylene-3,4,9,10-tetracarboxylic dianhydride and other cyclic anhydrides and imides according to the invention. Each cyclic anhydride and imide is identified and test data are given in the tables below.

TABLE 1

Test results for crude pigment compositions of Examples 1–7

| Example | Cyclic anhydride or imide | Masstone | | Undertone | | Metallic | |
|---|---|---|---|---|---|---|---|
| | | ΔC | Transparency | ΔH | ΔC | ΔH | ΔC |
| 1 | (b)(1) | −0.87 | 7.09 | 3.86 | 3.16 | 1.66 | 4.80 |
| 2 | (b)(2) | −3.14 | 5.70 | 4.05 | 1.79 | 2.03 | 3.06 |
| 3 | (b)(3) | 0.72 | 6.35 | 2.98 | 3.67 | 1.08 | 4.15 |
| 4 | (b)(4) | −2.06 | 2.02 | 1.8 | 0.84 | 0.82 | 1.12 |
| 5 | (b)(5) | −5.93 | 4.16 | 2.55 | −0.63 | 1.58 | −1.04 |
| 6 | (b)(6) | −4.22 | 5.82 | 1.93 | −0.04 | 0.96 | 0.74 |
| 7 | (b)(7) | −2.89 | 4.41 | 2.86 | 1.04 | 1.29 | 2.12 |

All values for ΔH, ΔC, and transparency are relative to untreated control. Positive values for ΔH, ΔC, and transparency correspond to yellower, more chromatic, and more transparent samples, respectively.

TABLE 2

Test results for milled pigment compositions of Examples 1–7

| Example | Cyclic anhydride or imide | Masstone | | Undertone | | Metallic | |
|---|---|---|---|---|---|---|---|
| | | ΔC | Transparency | ΔH | ΔC | ΔH | ΔC |
| 1 | (b)(1) | 1.24 | 11.13 | 4.32 | 3.54 | 1.32 | 6.29 |
| 2 | (b)(2) | −3.32 | 6.89 | 5.67 | 2.56 | 2.04 | 7.55 |
| 3 | (b)(3) | 3.67 | 10.71 | 3.84 | 4.41 | 0.86 | 7.56 |
| 4 | (b)(4) | −2.48 | 4.64 | 2.88 | 1.70 | 0.97 | 4.01 |

TABLE 2-continued

Test results for milled pigment compositions of Examples 1–7

| Example | Cyclic anhydride or imide | Masstone | | Undertone | | Metallic | |
|---|---|---|---|---|---|---|---|
| | | ΔC | Transparency | ΔH | ΔC | ΔH | ΔC |
| 5 | (b)(5) | −4.44 | 6.05 | 3.72 | 0.65 | 1.53 | 1.96 |
| 6 | (b)(6) | −2.73 | 4.51 | 1.75 | 0.58 | 0.39 | 1.60 |
| 7 | (b)(7) | −6.61 | 6.34 | 3.25 | −0.11 | 1.23 | 3.39 |

All values for ΔH, ΔC, and transparency are relative to untreated control. Positive values for ΔH, ΔC, and transparency correspond to yellower, more chromatic, and more transparent samples, respectively.

The data in the tables show that pigment compositions prepared according to the invention were yellower and more transparent than untreated pigment.

What is claimed is:

1. A process for preparing a perylene pigment composition comprising reacting
   (a) a perylene tetracarboxylic compound;
   (b) about 0.01 to about 20% by weight, relative to the perylene tetracarboxylic compound, of a non-pigmentary cyclic anhydride or imide having the formula

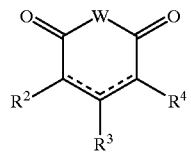

wherein
   W is O or $NR^1$,
   $R^1$ is hydrogen, a metal, $C_1$–$C_6$ alkyl, $C_5$–$C_8$ cycloalkyl, $C_7$–$C_{16}$ aralkyl, $C_6$–$C_{10}$ aryl, or -Alk-X,
   $R^2$, $R^3$, and $R^4$ are independently hydrogen, $C_1$–$C_6$ alkyl, $C_7$–$C_{16}$ aralkyl, or $C_6$–$C_{10}$ aryl, or $R^2$ and $R^3$ together are fused-on rings and $R^4$ is hydrogen, $C_1$–$C_6$ alkyl, $C_7$–$C_{16}$ aralkyl, or $C_6$–$C_{10}$ aryl, or $R^2$, $R^3$, and $R^4$ together are fused-on rings,
   the dotted line is an optional double bond representing $R^2$—C=C—$R^3$ or $R^3$—C=C—$R^4$,
   Alk is $C_1$–$C_{18}$ alkylene or $C_5$–$C_8$ cycloalkylene, and
   X is
      (i) an anionic group selected from —$SO_3^-$, —$COO^-$, —$PO_3^=$, —$PO(OR^x)O^-$ (wherein $R^x$ is $C_1$–$C_6$ alkyl), —O—$PO_3^=$, or —O—$PO(OR^y)O^-$ (wherein $R^y$ is $C_1$–$C_6$ alkyl), wherein the anionic group is electrically balanced with a stoichiometric amount of a cation,
      (ii) a cationic group having the formula —$NR^aR^bR^{c+}$ (wherein $R^a$, $R^b$, and $R^c$, are independently hydrogen, $C_1$–$C_6$ alkyl, $C_7$–$C_{16}$ aralkyl, or $C_6$–$C_{10}$ aryl), wherein the cationic group is electrically balanced with a stoichiometric amount of an anion,
      (iii) $NR^dR^e$, wherein $R^d$ is hydrogen, $C_1$–$C_6$ alkyl, $C_7$–$C_{16}$ aralkyl, $C_6$–$C_{10}$ aryl, $C_2$–$C_6$ alkanoyl, $C_7$–$C_{11}$ aroyl, or sulfonyl and $R^e$ is hydrogen, $C_1$–$C_6$ alkyl, $C_7$–$C_{16}$ aralkyl, or $C_6$–$C_{10}$ aryl,
      (iv) $OR^f$, wherein $R^f$ is hydrogen, $C_1$–$C_6$ alkyl, or $C_6$–$C_{10}$ aryl,
      (v) $COOR^g$, wherein $R^g$ is $C_1$–$C_6$ alkyl, $C_7$–$C_{16}$ aralkyl, or $C_6$–$C_{10}$ aryl, (vi) sulfonyl, or (vii) $C_6$–$C_{10}$ aryl;

(c) an equivalent excess, relative to the total amount of components (a) and (b), of ammonia or a primary amine having the formula $R^A$-$NH_2$ wherein $R^A$ is $C_1$–$C_6$ alkyl, $C_7$–$C_{16}$ aralkyl, or $C_6$–$C_{10}$ aryl;

(d) optionally, a solvent; and (e) optionally, one or more additives.

2. A process according to claim 1 wherein the perylene tetracarboxylic compound is a compound of the formula

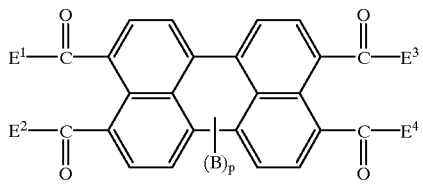

wherein $E^1$ and $E^3$ are independently OR or NR'R" and $E^2$ and $E^4$ are independently OR, or $E^1$ and $E^2$ together are O or $NA^1$ and $E^3$ and $E^4$ together are O or $NA^2$, each R is independently hydrogen, a metal or ammonium cation, $C_1$–$C_6$ alkyl, $C_7$–$C_{16}$ aralkyl, or $C_6$–$C_{10}$ aryl, each R' and R" is independently hydrogen, $C_1$–$C_6$ alkyl, or $C_7$–$C_{16}$ aralkyl, $A^1$ and $A^2$ are independently hydrogen, a metal, $C_1$–$C_6$ alkyl or substituted $C_1$–$C_6$ alkyl, $C_5$–$C_8$ cycloalkyl or substituted $C_5$–$C_8$ cycloalkyl, $C_7$–$C_{16}$ aralkyl or substituted $C_7$–$C_{16}$ aralkyl, or $C_6$–$C_{10}$ aryl or substituted $C_6$–$C_{10}$ aryl, B is $C_1$–$C_6$ alkyl, $C_1$–$C_6$ alkoxy, a sulfonyl group, amino, ammonium, hydroxy, nitro, or halogen, and p is zero or an integer of from 1 to 8.

3. A process according to claim 2 wherein, in the perylene tetracarboxylic compound, $E^1$, $E^2$, $E^3$, and $E^4$ are independently OH or a salt form thereof and B is absent.

4. A process according to claim 2 wherein the perylene tetracarboxylic compound is a bis-anhydride wherein $E^1$ and $E^2$ together and $E^3$ and $E^4$ together are oxygen atoms and B is absent.

5. A process according to claim 2 wherein the perylene tetracarboxylic compound is a bis-imide wherein $E^1$ and $E^2$ together and $E^3$ and $E^4$ together are independently each NH or a nitrogen atom substituted with $C_1$–$C_6$ alkyl, $C_7$–$C_{16}$ aralkyl, or $C_6$–$C_{10}$ aryl and B is absent.

6. A process according to claim 1 wherein, in the non-pigmentary cyclic anhydride or imide, $R^2$ and $R^3$ together form a fused-on hydrocarbon ring and $R^4$ is hydrogen.

7. A process according to claim 1 wherein, in the non-pigmentary cyclic anhydride or imide, $R^2$, $R^3$, and $R^4$ together form a fused-on polyaromatic ring.

8. A process according to claim 1 wherein the non-pigmentary cyclic anhydride or imide is a compound of the formula

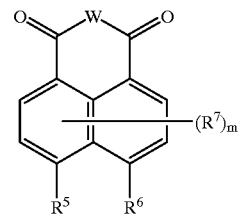

wherein

W is O or $NR^1$, $R^1$ is hydrogen, a metal, $C_1$–$C_6$ alkyl, or -Alk-X, $R^5$ and $R^6$ are independently hydrogen, $C_1$–$C_6$ alkyl, $C_1$–$C_6$ alkoxy, a sulfonyl group, amino, ammonium, hydroxy, nitro, or halogen, or $R^5$ and $R^6$ taken together are a group represented by the formula

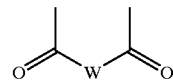

each $R^7$ is independently $C_1$–$C_6$ alkyl, $C_1$–$C_6$ alkoxy, a sulfonyl group, amino, ammonium, hydroxy, nitro, or halogen;

Alk is $C_1$–$C_{18}$ alkylene,

X is —$SO_3^-$ or —$COO^-$ electrically balanced with hydrogen or a stoichiometric amount of a metal ion; and m is zero or an integer of from 1 to 4.

9. A process according to claim 1 wherein component (b) is naphthalic anhydride or 1,4,5,8-naphthalenetetracarboxylic dianhydride.

10. A process according to claim 1 wherein component (b) is naphthalimide, N-methylnaphthalimide, N-(2-sulfoethyl) naphthalimide or a salt thereof, N-(2-sulfoethyl)-4-sulfonaphthalimide or a salt thereof, or N,N'-bis(2-sulfoethyl)-1,4,5,8-naphthalenetetracarboxylic diimide or a salt thereof.

11. A process according to claim 1 wherein component (c) is ammonia, a $C_1$–$C_6$ alkylamine, benzylamine, phenethylamine, aniline, anisidine, phenetidine, toluidine, or a xylidine.

12. A perylene pigment composition prepared by a process comprising reacting (a) a perylene tetracarboxylic compound;

(b) about 0.01 to about 20% by weight, relative to the perylene tetracarboxylic compound, of a non-pigmentary cyclic anhydride or imide having the formula

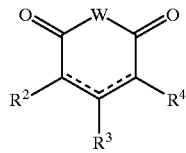

wherein

W is O or $NR^1$, $R^1$ is hydrogen, a metal, $C_1$–$C_6$ alkyl, $C_5$–$C_8$ cycloalkyl, $C_7$–$C_{16}$ aralkyl, $C_6$–$C_{10}$ aryl, or -Alk-X, $R^2$, $R^3$, and $R^4$ are independently hydrogen, $C_1$–$C_6$ alkyl, $C_7$–$C_{16}$ aralkyl, or $C_6$–$C_{10}$ aryl, or $R^2$ and $R^3$ together are fused-on rings and $R^4$ is hydrogen, $C_1$–$C_6$ alkyl, $C_7$–$C_{16}$ aralkyl, or $C_6$–$C_{10}$ aryl, or $R^2$, $R^3$, and $R^4$ together are fused-on rings, the dotted line is an optional double bond representing $R^2$—C=C—$R^3$ or $R^3$—C=C—$R^4$, Alk is $C_1$–$C_{18}$ alkylene or $C_5$–$C_8$ cycloalkylene, and X is
- (i) an anionic group selected from —$SO_3^-$, —$COO^-$, —$PO_3^=$, —$PO(OR^x)O^-$ (wherein $R^x$ is $C_1$–$C_6$ alkyl), —O—$PO_3^=$, or —O—$PO(OR^y)O^-$ (wherein $R^y$ is $C_1$–$C_6$ alkyl), wherein the anionic group is electrically balanced with a stoichiometric amount of a cation,
- (ii) a cationic group having the formula —$NR^aR^bR^{c+}$ (wherein $R^a$, $R^b$, and $R^c$, are independently hydrogen, $C_1$–$C_6$ alkyl, $C_7$–$C_{16}$ aralkyl, or $C_6$–$C_{10}$ aryl), wherein the cationic group is electrically balanced with a stoichiometric amount of an anion,
- (iii) $NR^dR^e$, wherein $R^d$ is hydrogen, $C_1$–$C_6$ alkyl, $C_7$–$C_{16}$ aralkyl, $C_6$–$C_{10}$ aryl, $C_2$–$C_6$ alkanoyl, $C_7$–$C_{11}$ aroyl, or sulfonyl and $R^e$ is hydrogen, $C_1$–$C_6$ alkyl, $C_7$–$C_{16}$ aralkyl, or $C_6$–$C_{10}$ aryl,
- (iv) $OR^f$, wherein $R^f$ is hydrogen, $C_1$–$C_6$ alkyl, or $C_6$–$C_{10}$ aryl,
- (v) $COOR^g$, wherein $R^g$ is $C_1$–$C_6$ alkyl, $C_7$–$C_{16}$ aralkyl, or $C_6$–$C_{10}$ aryl,
- (vi) sulfonyl, or
- (vii) $C_6$–$C_{10}$ aryl;

(c) an equivalent excess, relative to the total amount of components (a) and (b), of ammonia or a primary amine having the formula $R^A$-$NH_2$ wherein $R^A$ is $C_1$–$C_6$ alkyl, $C_7$–$C_{16}$ aralkyl, or $C_6$–$C_{10}$ aryl;

(d) optionally, a solvent; and (e) optionally, one or more additives.

* * * * *